Figure 3:
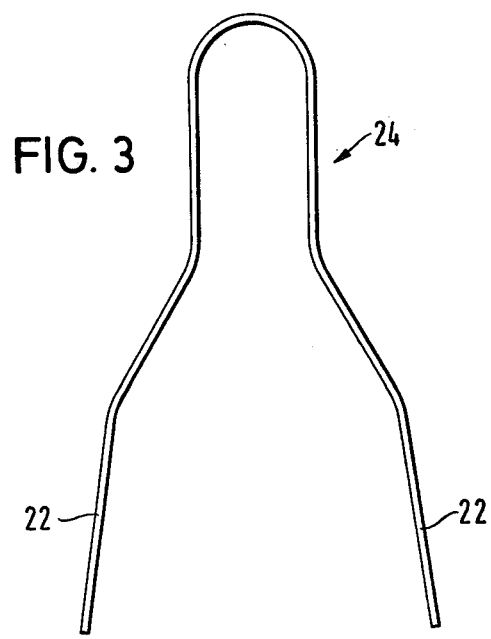

United States Patent [19]

Sturtzkopf

[11] 4,445,856

[45] May 1, 1984

[54] METHOD AND DEVICE FOR DETERMINING THE RELATIVE POSITION OF THE UPPER JAW AND LOWER JAW FOR THE PRODUCTION OF DENTURES

[76] Inventor: Robert Sturtzkopf, Wilhelm-Hey-Str. 14, Munich 60, Fed. Rep. of Germany

[21] Appl. No.: 344,300

[22] Filed: Feb. 1, 1982

[30] Foreign Application Priority Data

Oct. 2, 1981 [DE] Fed. Rep. of Germany ....... 3104721

[51] Int. Cl.$^3$ ............................................. A61C 9/00
[52] U.S. Cl. ...................................................... 433/71
[58] Field of Search ................................... 433/71, 46

[56] References Cited

U.S. PATENT DOCUMENTS

| | | | |
|---|---|---|---|
| 1,127,635 | 2/1915 | Kerr | 433/46 |
| 2,773,308 | 12/1956 | Van Court et al. | 433/71 |
| 3,161,956 | 12/1964 | Van Court et al. | 433/71 |
| 3,488,848 | 1/1970 | Lerman | 433/25 |

FOREIGN PATENT DOCUMENTS

| | | | |
|---|---|---|---|
| 2223937 | 12/1973 | Fed. Rep. of Germany | 433/71 |
| 2430702 | 1/1976 | Fed. Rep. of Germany | 433/71 |

*Primary Examiner*—Robert Peshock
*Attorney, Agent, or Firm*—Andrus, Sceales, Starke & Sawall

[57] ABSTRACT

A method and device for mutual alignment of the chewing surfaces of the upper jaw and the lower jaw for the purpose of producing dentures utilizes a wadding in the form of a bag filled with a freely shapeable, hardening material. The bag has a fork-like shape and is interposed between the upper jaw and the lower jaw. The material is allowed to harden once the chewing surfaces have been firmly closed on each other.

8 Claims, 3 Drawing Figures

METHOD AND DEVICE FOR DETERMINING THE RELATIVE POSITION OF THE UPPER JAW AND LOWER JAW FOR THE PRODUCTION OF DENTURES

The invention relates to a method and a device for determining the relative position of the upper jaw and the lower jaw for the production of dentures.

In order to produce dentures, such as dental prostheses, bridges and crowns precisely, it is necessary to achieve the most accurate reproduction possible of the position of the lower jaw in relation to the upper jaw in order to make it possible for the chewing surfaces to fit tightly together when closed after insertion of the denture.

In this context, several methods for registration of the spatial relation between the lower jaw and the upper jaw are known. In order to make a prosthesis for the toothless patient, according to the conventional methods, a provisional prosthesis is made for the lower jaw and a provisional prosthesis is made for the upper jaw, onto which wax rims are applied in place of the future teeth. First of all, the wax rim of the upper jaw prosthesis is ground down or heightened by additional application of wax with repeated checking of the prosthesis in the patient's mouth until the chewing surface of the wax rim is at the occlusal plane. The occlusal plane is a skull-related plane which is independent of tooth loss. Following this, the lower jaw prosthesis is inserted and its wax rim is also ground down or heightened with continuous checking of the prosthesis in the patient's mouth until its chewing surface has reached the correct height and fits snugly against the chewing surface of the upper jaw prosthesis when the jaws are closed.

When this point has been reached in the treatment, the attempt is made to instruct the patient to close his or her lower jaw correctly and in a relaxed position, i.e. not shifted to the front or to the side. If the dentist gains the impression that the patient is biting in the correct lower jaw position, then the lower jaw and the upper jaw prostheses are welded together by melting the wax rims and are removed from the mouth of the patient together. This mould is than used to make the final prosthesis.

This known method contains several error sources. For instance, the temporo mandibular joint is not a pure rotary joint. The lower jaw can in fact slide in the joint socket of the upper jaw and change its position. Besides this, both jaw joints and also the mucosa cushion, on which the provisional prostheses rest in the mouth, are tangibly compressible. It is therefore possible that a tight fit of the wax rims, when the jaws are closed, is only simulated when the wax rims are fitted on, since the insufficient parallelism and the mutual alignment of the chewing surfaces are compensated for in a hardly controllable manner due to the adjustment of the joint and the above mentioned compressibility.

It is also difficult in many cases for the patient to close his or her jaws in the required correct position 'blindly', i.e. without the possibility of correction through contact with the upper jaw as is the case with people with a normal set of teeth. However, as soon as the wax rims of the upper jaw prosthesis and the lower jaw prosthesis come into contact with each other as a result of biting and the position correction strived for by means of the muzzles through sliding into position of the chewing surfaces, this position correction is prevented by the friction of the two wax rims against each other. The conclusion derived from all this is that it is tiresome and time-consuming to fit the wax rim of the lower jaw prosthesis in such fashion that it really has a tightly fitting contact with the wax of the upper jaw prosthesis when the jaws are closed.

An improved and also known method consists of bringing the upper jaw prosthesis and the lower jaw prosthesis into contact at one point only when biting. A supporting pin which protrudes towards the tongue, is fixed to the centre of gravity, i.e. the gum centre of the upper jaw prosthesis. This pin is faced by a recording plate which is attached to the lower jaw prosthesis. When the patient bites, the pin contacts the plate without the wax rims touching. All the other procedures are analogous to those of the first mentioned method. The advantages of this method are the uniform load applied to the jaw joints and the uniform impression of the mucosa carrying the prostheses. The disadvantages are that this method is time consuming and that it, too, does not provide faultless position correction of the lower jaw after contact with the upper jaw (i.e. unhindered interaction between the jaw joints and the muzzles is not possible here, either), since this is prevented by the friction of the supporting pin against the recording plate.

In the case of patients with a full set of teeth, another known method for making bridges and crowns is to use a bite plate which essentially consists of a heated wax plate which is placed onto the teeth, whereupon the patient is allowed to bite. In this case, as well, the position correction of the lower jaw, as would correspond to the unhindered interaction of jaws and muzzles, is not possible. The reason for this is that, as soon as the upper-jaw tooth side and the lower-jaw tooth side come into contact, the interposed wax plate prevents unhindered sliding. The same applies analogously to the production of a wax bite in orthodontics.

The objective of the present invention is thus to provide a method and a device by means of which mutual alignment of the chewing surfaces of the upper jaw and the lower jaw can be achieved with great precision at a reduction of time and work required.

This objective is achieved in this invention by means of a method according to which a freely shapable wadding is inserted between the upper jaw and the lower jaw and is allowed to harden after the chewing surfaces have firmly closed on each other. The advantage of the method is that the soft and freely shapable wadding is inserted into the patient's mouth for taking a bite in such fashion that it comes to rest between the prostheses or between the teeth when the patient bites. When the patient bites, the wadding yields flexibly so that the patient can determine the correct position of the upper jaw and the lower jaw by simple, relatively firm biting until the wadding has hardened.

The wadding is formed in the position thus determined and is then allowed to harden so that the shape of the hardened wadding corresponds exactly to a firm fit of the chewing surfaces.

A further advantage of the wadding is the fact that the provisional lower jaw prosthesis and upper jaw prosthesis are both pressed against the oral mucosa in uniform fashion. Moreover, an identical load is applied to both jaw joints when the patient bites since the wadding is flexibly deformable. The position of the lower jaw corresponding to unhindered interaction between the jaw joints and the muzzles can be adjusted faultlessly by means of the flexible contact with the upper jaw. In addition to this, the time consuming paralleling of the provisional lower jaw prosthesis in relation to the provisional upper jaw prosthesis, in order to achieve closely fitting chewing surfaces, is no longer required.

This invention provides a device for carrying out the method which consists of a bag filled with a deformable and hardening material. Basically a soft and deformable material which hardens after a prespecified time is suitable as wadding. However, for this invention, a prepared bag which is filled with a deformable and hardening material at the appropriate moment is particularly expedient. The bag can be filled with a hardening plastic. An especially uncomplicated method is to fill the bag with stirred gypsum which hardens within a short period of time and provides an impression with especially clearly defined contours.

Taking a bite impression from a patient with teeth is carried out in analogous fashion with the wadding or bag alone, while the wax rims and provisional prostheses are, of course, omitted in this case.

Figure 1:
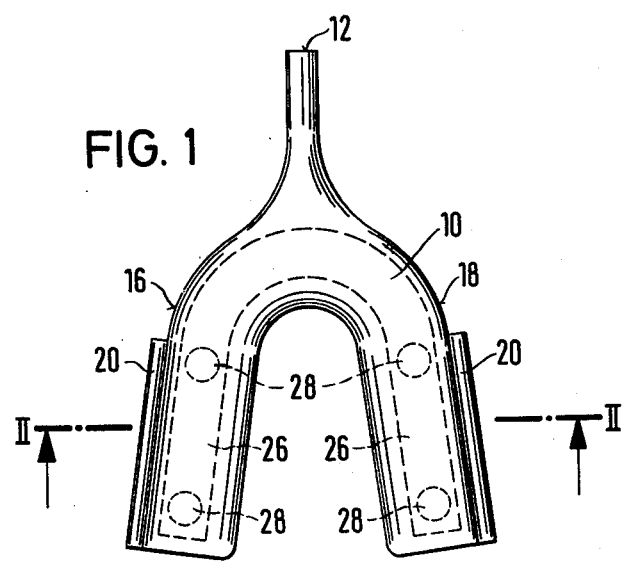

The invention is described in detail below by means of the diagrams. These diagrams include the following:

FIG. 1: a top view of the bag

Figure 2:
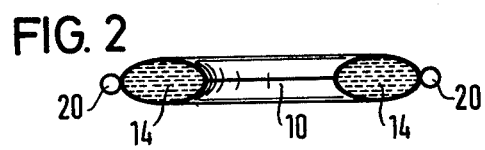

FIG. 2: a sectional view of the bag taken along the line II—II of FIG. 1

FIG. 3: a holder for the bag.

As can be seem from the diagram, the wadding consists of the bag 10 which e.g. consists of two thin plastic foils which are connected to each other by means of welding along their edges. A filling opening 12 protrudes in tubular fashion and is used for filling the hardening liquid into the bag by means of a syringe. FIG. 2 shows the bag 10 filled with the liquid 14.

There are pockets 20 formed on both outer longitudinal edges 16,18 of the bag, into which the shanks 22 of the holder 24 are inserted.

In the case of patients without teeth, the provisional upper jaw prosthesis is made in the conventional fashion with the wax rim and is then fitted in, i.e. the chewing surface is created as reference surface with relation to the skull. The wax rim of the lower jaw prosthesis is reduced in height by approximately the thickness of the bag which will subsequently rest upon it. Once the sachet has been attached to the holder, the bag 10 is filled with hardening liquid, such as gypsum, through the filling opening 12 and the holder with the bag is inserted between the upper jaw and the lower jaw. In doing so, the filling opening is squeezed together so that no liquid can escape. This is followed by the patient biting during which the correct height of the lower jaw prosthesis can be controlled by letting the appropriate amount of liquid run out of the bag through the filling opening 12 during biting. Once the correct height has been reached, the opening is closed and the dentist waits until the liquid has hardened. The correct position of the lower jaw in relation to the upper jaw is registered in this fashion. The wax rims of the upper jaw and of the lower jaw have impressed themselves in the bag. A particularly expedient procedure is to form projections spaced along the wax rims of the upper jaw and of the lower jaw which impress themselves into the bag when the patient bites. The wax rims and the projections leave a mould in the bag, so that the position of the chewing surfaces of the upper jaw and of the lower jaw can be exactly reconstructed outside of the nouth as well by means of the interposed hardened bag.

In FIG. 1, the impression of the wax rim of the upper jaw chewing surface is listed as 26 and the impressions of the projections on the wax rim of the upper jaw are listed as 28.

I claim:

1. A device suitable for use with upper and lower jaw prostheses for determining the mutual alignment of dentally significant surfaces of the upper and lower jaws of a patient comprising: an arcuate bag, a wadding formed of a freely shapeable, hardenable material (14) contained in said bag; and holding means connected to said bag independently of the prostheses for inserting the bag between the prostheses, said holding means comprising tubular pockets (20) positioned on the exterior of said arcuate bag in a central plane of said bag lying generally parallel to the upper and lower jaws of the patient, said holding means further comprising a wire handle (24) having a central gripping portion and a pair of spaced shank portions (22) insertable in said pockets.

2. Device as described in claim 1 characterized by the fact that the bag (10) is filled with a hardening plastic material.

3. Device as described in claim 1 characterized by the fact that the bag (10) is filled with a hardening liquid.

4. Device as described in claim 3 characterized by the fact that the bag (10) is filled with gypsum.

5. Device as described in one of claims 1–4 characterized by the fact that the bag (10) is a plastic sachet with a filling opening (12).

6. Device as described in claim 5 characterized by the fact that the filling opening is elongated in a tubular shape.

7. Device as described in one of claims 2–6 characterized by the fact that the bag has a fork-like shape and that the filling opening is located at the centre as an elongation of the shanks.

8. A method for determining the mutual alignment of dentally significant surfaces of the upper jaw and the lower jaw of a patient comprising the steps of:
fitting provisional upper and lower jaw prostheses into the mouth of a patient;
positioning a freely shapeable, hardenable wadding having a generally arcuate form between the upper and lower jaw prostheses independently of the fitting of the protheses; said positioning being carried out by means of a handle having shank portions removably attached to the arcuate wadding;
registering the correct position of the lower jaw in relation to the upper jaw with respect to proper vertical, horizontal, and angular relationship by firmly closing the patient's jaws on the wadding and horizontally sliding of the lower jaw with respect to the upper jaw;
allowing the wadding to harden with the jaws in the correct position; and
removing the hardened wadding, and thereafter the jaw protheses, from the mouth of the patient.

* * * * *

UNITED STATES PATENT AND TRADEMARK OFFICE
CERTIFICATE OF CORRECTION

PATENT NO. : 4,445,856
DATED : May 1, 1984
INVENTOR(S) : ROBERT STURTZKOPF

It is certified that error appears in the above-identified patent and that said Letters Patent is hereby corrected as shown below:

Column 2, Line 5,     after "wax", insert ---rim---

Column 4, Line 3,     cancel "nouth" and insert ---mouth---

Column 4, Line 32,    cancel "one of claims 1-4" and insert ---claim 1---

Column 4, Line 38,    cancel "one of claims 2-6" and insert ---claim 6---

Signed and Sealed this

Twelfth Day of February 1985

[SEAL]

Attest:

DONALD J. QUIGG

Attesting Officer     Acting Commissioner of Patents and Trademarks